(12) United States Patent
Born et al.

(10) Patent No.: US 7,173,127 B2
(45) Date of Patent: Feb. 6, 2007

(54) METHOD FOR THE MANUFACTURE OF CAPROLACTAM FROM WASTE CONTAINING POLYAMIDES

(75) Inventors: Claus Born, Ingelheim (DE); Rudolf Kämpf, Gründau (DE); Joachim Seelig, Biebergemünd (DE); Reinhard Wolf, Rodenbach (DE)

(73) Assignee: Zimmer Aktiengesellschaft, Frankfurt am Main (DE)

( * ) Notice: Subject to any disclaimer, the term of this patent is extended or adjusted under 35 U.S.C. 154(b) by 199 days.

(21) Appl. No.: 10/457,831

(22) Filed: Jun. 9, 2003

(65) Prior Publication Data

US 2004/0024204 A1 Feb. 5, 2004

(30) Foreign Application Priority Data

Jun. 10, 2002 (DE) ................. 102 25 692

(51) Int. Cl.
*C07D 201/16* (2006.01)
(52) U.S. Cl. ..................................... 540/540
(58) Field of Classification Search ................ 540/540; 260/239
See application file for complete search history.

(56) References Cited

U.S. PATENT DOCUMENTS

| | | | |
|---|---|---|---|
| 2,752,336 A | | 6/1956 | Boon et al. |
| 2,813,858 A | * | 11/1957 | Joris ........................... 540/540 |
| 3,839,324 A | * | 10/1974 | Schultze et al. ............. 540/540 |
| 3,977,952 A | | 8/1976 | Knoevenagel et al. |
| 4,107,160 A | | 8/1978 | Dicoi et al. |
| 4,148,792 A | | 4/1979 | Danziger et al. |
| 4,605,672 A | | 8/1986 | Toth et al. |
| 5,359,062 A | | 10/1994 | Fuchs et al. |
| 5,598,980 A | | 2/1997 | Dilly-Louis et al. |
| 5,637,700 A | | 6/1997 | Fuchs et al. |
| 5,656,757 A | * | 8/1997 | Jenczewski et al. ........ 540/540 |
| 5,990,306 A | | 11/1999 | Mayer et al. |
| 6,056,633 A | | 5/2000 | Sesena et al. |
| 6,095,441 A | | 8/2000 | Unkelbach et al. |
| 6,111,099 A | | 8/2000 | Frentzen et al. |
| 6,187,917 B1 | | 2/2001 | Mayer et al. |
| 6,579,979 B2 | | 6/2003 | Leconte |
| 2002/0030014 A1 | | 3/2002 | Leconte |

FOREIGN PATENT DOCUMENTS

| | | |
|---|---|---|
| DE | 887 199 | 8/1953 |
| DE | 889199 | 9/1953 |
| DE | 1105420 | 4/1961 |
| DE | 2408778 | 9/1975 |
| DE | 24 16 573 | 10/1975 |
| DE | 25 07 744 | 9/1976 |
| DE | 19 719 734 | 11/1998 |
| EP | 910 056 | 4/1954 |
| EP | 0 676 394 | 10/1995 |
| EP | 0 681 896 | 11/1995 |
| EP | 0 875 504 | 11/1998 |
| EP | 0 875 505 | 11/1998 |
| EP | 0 876 847 | 11/1998 |
| IN | 142150 | 6/1977 |
| JP | 5313636 | 11/1993 |
| JP | 8099954 | 4/1996 |
| JP | 2000038377 | 2/2000 |

OTHER PUBLICATIONS

Brandup, et al., "Die Wiederverwertung von Kunststoffen", (The Recycling of Plastics), Verlag Carl Hanser Munich, Vienna, 1995, pp. 513-520.
Organikum, Organisch-chemisches Grundpraktikum, Veb Deutscher Verlag der Wissenschaften, Berlin 1988, pp. 54-59.

* cited by examiner

*Primary Examiner*—Bruck Kifle
(74) *Attorney, Agent, or Firm*—Michael Best & Friedrich LLP

(57) ABSTRACT

This invention relates to a continuous and efficient method for the manufacture of highly pure caprolactam suitable for the polycondensation of Polyamide 6 (polycaprolactam) from polyamide waste. In particular the invention relates to a method for the manufacture of caprolactam from waste containing polyamides, including the steps a) depolymerisation of the waste containing polyamides, whereby a caprolactam raw material and a flow containing secondary constituents or additives is obtained, b) at least one distillation of the caprolactam raw material, and c) at least one crystallisation of the caprolactam material obtained in step b), by which means caprolactam is obtained, whereby at least part of the caprolactam obtained in step c) with a permanganate number of<10000 sec. and a UV transmission of<85% is added to the waste containing polyamides before and/or during the depolymerisation.

15 Claims, 2 Drawing Sheets

METHOD FOR THE MANUFACTURE OF CAPROLACTAM FROM WASTE CONTAINING POLYAMIDES

FIELD OF THE INVENTION

This invention relates to a continuous and efficient method for the manufacture of highly pure caprolactam suitable for the polycondensation of Polyamide 6 (polycaprolactam) from polyamide waste.

BACKGROUND OF THE INVENTION

With clean, freshly made polyamides which have not been subjected to auxiliary processing, processing to products with quality features such as possessed by new goods is quite easily possible. However, if articles of daily use which have been used for many years or products from a collection of plastics are to be recycled, this can only be carried out with a highly technical, energy-consuming and expensive effort.

Here, cleaning and sorting stages are necessary to obtain sorted material, because plastic products are always matched to the field of application and therefore contain additives, colorants, stabilisers, glass fibre, etc. specific to the manufacturer or manufacturing process and which make processing difficult. Consequently, with the economical recycling of polyamide waste, cracking into the monomers is essential if a product is to be produced which is indiscernible from products manufactured from monomers through the synthesis route.

Caprolactam is the monomer which is used to manufacture Polyamide 6 from which parts for vehicles and injection moulded parts with glass fibre and other additives are made and from which fibres for yarn are spun that are used in carpets and carpet floor covering materials or other objects used in daily life.

A large part of this material is fed into plastics circulation after the intended use of the products and is reused via plastics recycling. Since the Polyamide 6 products are usually not the sole material containing amide groups, but rather polyamides are also present which consist of various diacids and diamines, identification and sorting into the individual polyamide product groups must take place. If this separation does not take place, then substantial problems due to mixed reactions of the various monomer groups, yield losses due to byproducts and insufficient quality must be expected with the monomer obtained. The major share of the Polyamide 6 plastic material, for example, goes into the manufacture of fibres and in particular into applications in floor coverings. The Polyamide 6 is spun to form fibres which are needled in carpet factories to form a backing fabric, e.g. polypropylene fleece, and are processed to looped or velour fabrics depending on the type of carpet. After needling of the yarn, which is pulled off bobbins, onto the backing fabric, the pile is fixed by an adhesive layer onto which a polymer foam backing is then applied which is filled with a filling material, such as chalk. One purpose which the foam backing fulfils is to efficiently deaden footsteps and also to produce the necessary weight so that the carpet lies flat on the floor without gluing.

The processing of Polyamide 6 waste after the intended use has been described in various patents, such as for example DE 19719734, EP 0681896, U.S. Pat. No. 5,598,980, DE 2416573 and DE 2507744 and includes the detection and sorting of non-polyamide 6 products, their crushing and the separation of dirt and other types of additives. For the separation of individual components such as they occur, for example, in the crushing of carpets in the form of foam backing, pile and supporting material, multi-stage floatation and sedimentation processes are preferably employed, followed by centrifuges and salt solutions of various densities to cause the lighter fraction, such as polypropylene fabric, to float and the heavy, filled carpet backing to form the sediment. A Polyamide 6 fraction obtained in this way is freed from salt by washing and is dried in a continuous process and then passed to depolymerisation via an extruder. In the depolymerisation, methods are followed, for example, according to those known from DE 887 199, EP 0875504, DE 910056, U.S. Pat. No. 4,605,762 and JP 53-13636, in which, using phosphoric acid, breaking down of the polymer chains takes place and where introduced steam drives off the produced caprolactam as a water-steam mixture.

Furthermore, a method for the manufacture of purified caprolactam from a carpet containing polyamides is known from U.S. Pat. No. 5,990,306 in which the caprolactam is distilled and crystallised after depolymerisation.

In addition, a method for the continuous recovery of caprolactam from polycaprolactam waste is known from U.S. Pat. No. 4,107,160, whereby, among others, a caprolactam-water mixture which is obtained through the distillation of the caprolactam, is mixed with fresh water vapour and passed to depolymerisation as a superheated mixture.

The obtaining of highly pure caprolactam from Polyamide 6 waste, such as from used carpets or the other products mentioned above, is continuously subject to variations in the composition of the flow of input material. Consequently, on one hand, the secondary constituent components of a carpet, such as foam backing or backing fabrics, vary depending on the manufacturer and on the other hand, the Polyamide 6 is differently mixed with additives and colorants, etc. Therefore, a non-uniform and continuous supply of raw materials prevails. To manufacture a highly pure product from a material with such extreme variation in the input products and which meets or exceeds the quality requirements of the synthesized caprolactam is an objective not yet achieved on a large scale.

A disadvantage with the known methods of processing Polyamide 6 waste is therefore that they do not supply any highly pure caprolactam which can be used for manufacturing Polyamide 6.

SUMMARY OF THE INVENTION

In one aspect, the invention may provide a method for the manufacture of caprolactam from waste containing polyamides. The method may comprise:
 a) depolymerisation of the waste containing polyamides to obtain a flow containing caprolactam raw material and, where applicable, a flow containing secondary constituents or additives,
 b) at least one distillation of the caprolactam raw material, and
 c) at least one crystallisation of the caprolactam material obtained in step b) to obtain at least one caprolactam,
  whereby at least part of the caprolactam obtained in step c) with a permanganate number of<10000 sec. and a UV transmission of<85% is added to the waste containing polyamides before and/or during the depolymerisation.

DETAILED DESCRIPTION OF THE INVENTION

The method according to the invention is particularly preferably carried out continuously. The invention may provide a method for the manufacture of caprolactam from waste containing polyamides, the said method may be economical and simple to implement and with which a highly pure caprolactam can be manufactured, suitable for polycondensation to a high quality product which cannot be differentiated from products of Polyamide 6 manufactured from industrial caprolactam.

The material containing polyamides is preferably selected from the group consisting of moulded parts containing polyamides, such as parts for vehicles, injection moulded parts containing polyamides with glass fibre and other additives as well as fibres, carpets, carpet floor coverings containing polyamides and other objects from everyday life containing polyamides, such as clothing. The material containing polyamides which is passed to the depolymerisation may also contain non-polymers and other types of additives.

The waste containing polyamides is preferably first sorted before the depolymerisation is carried out, so that it mainly contains Polyamide 6 and the other remaining materials are separated as described above.

In addition, the waste containing polyamides is preferably compacted and melted before depolymerisation.

The depolymerisation is preferably carried out at a temperature of about 180° C. to about 300° C. and at pressures of about 0.5 bar to about 2 bar, as described in DE 887199, EP 0 875 504, DE 910056, U.S. Pat. Nos. 4,605,762, 5,990,306 and JP 53-13636. In addition, a basic or acidic catalyst, such as phosphoric acid, is preferably added. The reaction conditions during the depolymerisation are preferably adapted to the varying composition of the raw material added to the process, i.e. the waste containing polyamides. The steam temperature can, for example, be increased, greater quantities of steam used, the mol ratio of the phosphoric acid to polyamide changed and/or the pressure increased or reduced.

Figure 1:
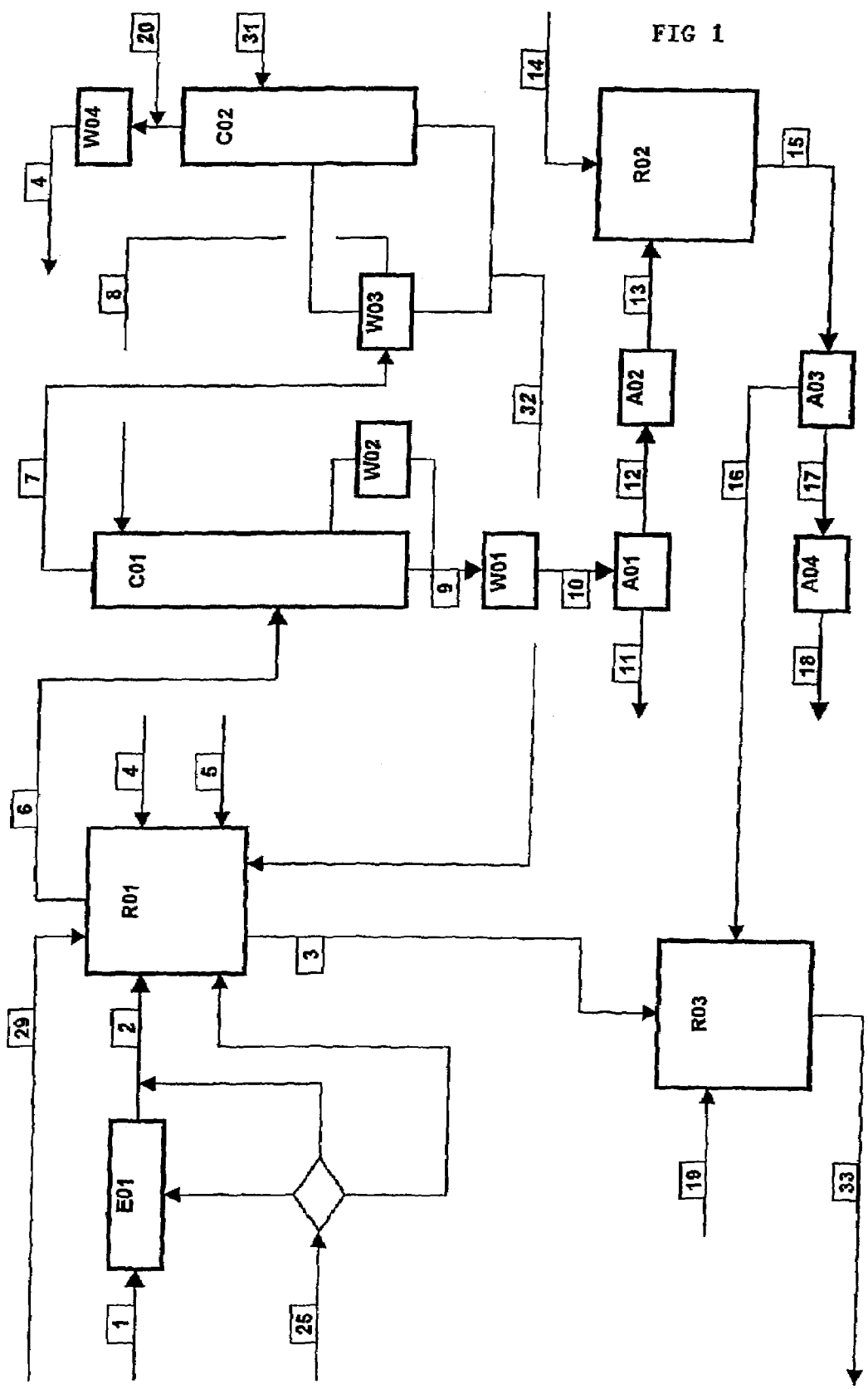
FIGS. 1 and 2 show schematically a plant for carrying out a preferred embodiment of the method according to the invention.
Figure 2:
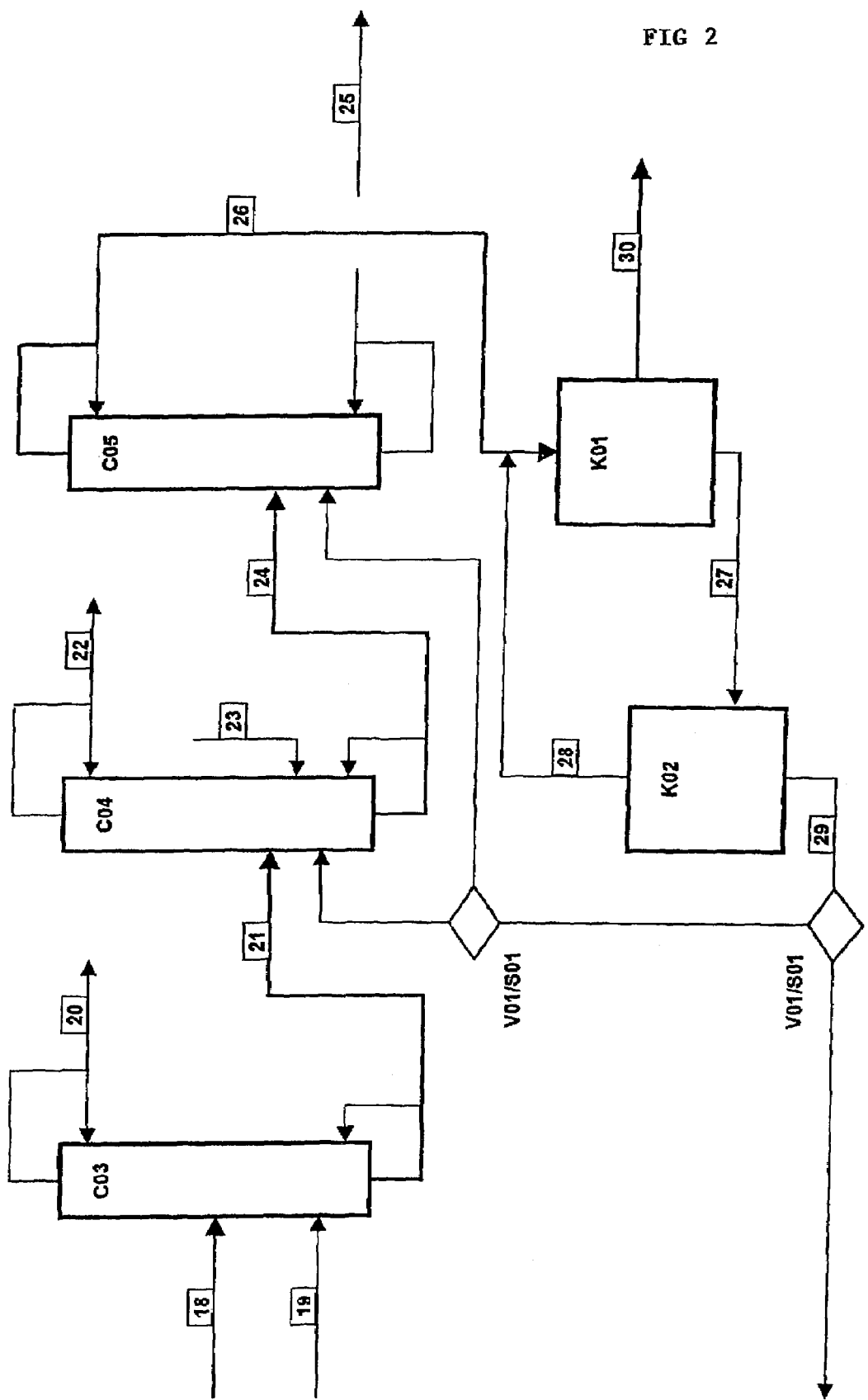

After depolymerisation, in the method according to the invention at least one distillation is carried out as described in FIGS. 1 and 2. The terms "distilling" and "distillation" are here used generally for distilling, fractional distillation and purification stages as carried out in columns or plants, for example in vacuum columns, extraction columns, concentration columns, rectification columns and refraction columns (see FIGS. 1 and 2).

Preferably, at least four distillations are carried out whereby with the first distillation, as in apparatus C01, the raw lactam/water mixture is concentrated. After running through a number of separation and refining stages, the raw caprolactam concentrate enters the second distillation, as in the evaporation plant C03, where water is driven off and another concentration occurs. Neutralisation of the acidic components occurs here through the addition of alkali. The third distillation, as in the distillation plant C04, has the task of stripping off constituents with a lower boiling point than caprolactam under the addition of nitrogen containing ammonia. After leaving the third distillation, as in the distillation plant C04, the raw caprolactam enters the fourth distillation, such as the distillation plant C05, where, under reduced pressure, a distilled pure caprolactam is drawn off at the top. Since this however does not fulfil the criteria for a high purity product, it is passed to the at least one crystallisation, such as the fractionating crystallisation K01/K02.

In addition the cracking caprolactam-water mixture escaping from the depolymerisation in the vapour phase is passed to a first distillation (evaporation) in which the escaping and energetic vapours can be used to heat and evaporate the water arising from the Polyamide 6 granulate extraction and which still contains monomers and oligomers, whereby the energy-rich vapours condense and are passed as reflux to the evaporation stage. The vapours from the first caprolactam distillation, which still contain caprolactam according to the vapour pressure equilibrium and are only partially condensed, can be used in this way. The partial condensation at the level of the required quantity of the reflux ratio and the use of the energy content of the remaining vapours in the depolymerisation are advantageous. In addition the steam from the polyamide extraction concentration, as in plant C05, can be returned to the depolymerisation.

The vapours emitted from the extract-water evaporation C02 and the raw caprolactam distillation C03 can also be passed advantageously to a superheater. The superheated steam that is then produced can be passed to the depolymerisation for breaking down the polymer chains.

In particular it has been found to be economically advantageous to recirculate before and/or to the depolymerisation a distillation residue, which originates from a distillation plant, following the depolymerisation (vacuum column), for purifying the caprolactam in the method for manufacturing caprolactam from waste containing polyamides, and which, apart from short-chain polymers, colorants and products from secondary reactions, still contains utilisable quantities of caprolactam, as described below also based on FIGS. 1 and 2.

This method has proved to be particularly advantageous when melting the material containing polyamides precedes the depolymerisation and the melting of the waste containing polyamides occurs under vacuum. With regard to the polymer breakdown and the energy consumption, a further method has proved to be economically more advantageous compared to the one described above if a residue from a vacuum column (distillation plant for purifying the caprolactam) occurs during melting at a point in an extruder for melting such that the vapours going into the vacuum are not loaded. This can, for example, occur in the condensation zone. The added residue from the vacuum column reduces the melt viscosity, promotes the breakdown of the polymer chains and thus makes the transport easier through the extruder for a low driving force.

In the method according to the invention preferably at least two crystallisation stages are carried out, whereby both stages are carried out preferably as fractionated. Here, the desired product, i.e. high purity caprolactam, is first separated and after an analysis is either stored for the manufacture of polyamide or is passed again to depolymerisation, distillation and/or crystallisation as described below based on FIGS. 1 and 2.

In the method according to the invention a fractionating crystallisation melt process is applied at least once.

It is also advantageous if the crystallised caprolactam which is obtained from the at least one crystallisation is preferably subjected, after an initial purification stage of the fractionating crystallisation melt process, to a continuous analysis such as permanganate number, UV transmission, APHA number, alkalinity and volatile base content to achieve a quality at least equivalent to a synthesized caprolactam.

The caprolactam obtained after step c) with a permanganate number of <10000 sec. and a UV transmission of <85%

(also termed reflux caprolactam), preferably with a permanganate number of <8000 sec. and a UV transmission of <82%, which is added to the material containing polyamides before and/or during the depolymerisation, is a caprolactam which does not fulfil the criteria for a high purity product which is suitable for the production of Polyamide 6 polycondensates of the best quality. One aspect of the reflux of this caprolactam in the method according to the invention is that it promotes the breakdown of the material containing polyamides.

Preferably, the complete caprolactam obtained after step c) with a permanganate number of <10000 sec. and a UV transmission of <85% is added before and/or during the depolymerisation.

In addition preferably at least part of the caprolactam obtained in step c) with a permanganate number of <10000 sec. and a UV transmission of <85%, but preferably with a permanganate number of <8000 sec. and a UV transmission of <82% can be added in step b).

Especially preferably, the caprolactam obtained from step c), the crystallisation, can be added either again to the depolymerisation, distillation or again to the crystallisation in dependence of its purity.

Preferred in particular, caprolactam, which exhibits quality features of APHA>5, UV transmission<80, permanganate number<5000 sec., alkalinity>1 mmol/kg, volatile bases>1 mmol/kg, is returned advantageously to the depolymerisation. Caprolactam with values APHA>3, UV transmission<82%, permanganate number<8000 sec., alkalinity 0.5 mmol/kg, volatile bases 0.5 mmol/kg is advantageously passed to one of the distillation stages and caprolactam with APHA 4, UV transmission 85%, permanganate number 10000 sec., alkalinity 0.5 mmol/kg and volatile bases 0.5 mmol/kg is preferably passed to the crystallisation.

Furthermore, when carrying out the method according to the invention, preferably secondary constituents and additives of the material which is used containing polyamides, such as SBR foam backing, chalk, soot and fabric residues, are continuously discharged after the depolymerisation through analysis and monitoring of the acid and nitrogen content of the flow containing the additives, supervised and controlled in dependence of the nitrogen content and catalyst content, for example, phosphoric acid.

It has proven advantageous to maintain the phosphoric acid content in the discharge between 0.1% of mass and 50% of mass, but it is particularly advantageous between 1% of mass and 25% of mass. The nitrogen content is advantageously between 0.1% of mass and 10% of mass, but particularly advantageous between 1% of mass and 5% of mass.

In particular, the analysis and monitoring of the cracking acid and nitrogen content of the flow, which contains the additives and secondary constituents and leaves the depolymerisation, is advantageously carried out continuously, because the composition of the raw material fed into the process, i.e. the waste containing polyamides, continually changes.

In addition, it is preferable if the raw caprolactam concentrate from a first distillation (evaporation C01) is examined through continuous analyses for its quality features such as permanganate number, UV transmission, APHA number, alkalinity and volatile base content.

Preferably the raw caprolactam has the following minimum properties: APHA>4, UV transmission<82, permanganate number<8000 sec., alkalinity>0.5 mmol/kg, volatile bases>0.5 mmol/kg. If the values do not correspond to the analyses of a desired caprolactam produced industrially by the synthesis method, it is advantageous to pass the operating conditions in C01–C05, R02 and K01, K02 and the quality features such as permanganate number, UV transmission, APHA number, alkalinity and volatile base content to a memory with correlations of operating conditions and quality features being determined by neuronal network software and these are used for the open and closed loop control of the distillation (evaporation) in the most efficient range. In addition, their constants are found from linked linear and non-linear high order equation systems using equation solvers. An important point is also represented by the performance characteristics in which relationships of the product quality on the basis of the process conditions are acquired, as they are similarly known from the automotive industry for engine control. The important features of this closed-loop control are that, for example, with the undercutting of the UV transmission value the vapour temperature reduces, with an increase in the alkalinity and volatile base content the phosphoric acid concentration increases and with an increase in the permanganate number the cracking vapour or pressure in the depolymerisation reactor is reduced. In the distillation columns C01–C05 a reduction or increase of the pressure occurs in dependence of the deviation of the criteria which are to be placed on a high purity caprolactam. An increase in the reflux ratio or a lowering of the temperature is carried out when the colour values worsen.

In the method according to the invention it is preferable to add additives and/or oxidation agents in a refining stage to the caprolactam obtained after step b). If more than one distillation is carried out in step b), then the additives and/or oxidation agents can be added at least once to the caprolactam obtained after the first and before the last distillation. Preferably, the additives and/or oxidation agents are added after the first distillation.

It is particularly preferable to pass the raw caprolactam concentrate from the distillation (evaporation C01) through at least one separator before and after the distillation for treatment with additives and/or oxidation agents to improve the quality characteristics such as permanganate number, UV transmission, APHA number, alkalinity and volatile base content. Here, the addition of additives and/or oxidation agents to the raw caprolactam concentrate in a refining step can be monitored and the added quantity be controlled by continuous analysis on account of the non-uniform raw material composition of the input product, i.e. the waste containing polyamides. The dosage of an oxidation agent, such as aqueous potassium permanganate solution, occurs in dependence of the UV transmission and the APHA number and must be arranged such that more permanganate is added when the colour worsens.

For example, if the UV transmission falls below 85% an adsorption agent is added, such as for example active carbon, and below a limit of 66% another auxiliary agent is added, such as diatomaceous earth.

This control is not constant, but is instead proportional to the changes, because the disturbance substances applied with the raw material determine the amounts to be added and a constant product quality can only be ensured in this way, which is why the product properties are measured. In this way the least possible additive can be used to achieve the greatest possible effect and overdosage or underdosage as a consequence of the varying raw material composition can be prevented, because this in turn causes increased costs and impaired product quality. In the following purification stages stricter/closer operating conditions can then be applied to compensate for these product quality impairments.

In addition, a packed bed filtration of the obtained caprolactam can be carried out preferably after step b). If more than one distillation is carried out in step b), a packed bed filtration can be carried out after at least one distillation. Here, the packed bed filtration is particularly preferably carried out after the first distillation. If additives and/or oxidation agents are added to the caprolactam after or during step b), a packed bed filtration can be carried out before and/or after they are added.

For the efficient usage of waste heat and the reduction of water consumption the vapours from a first or second distillation (evaporation C03) can be only partially condensed in a quantity such that the reflux amount is ensured and the remaining non-condensed and hot vapours can be used after superheating as cracking steam during the depolymerisation.

It is also preferable with the at least one distillation (evaporation) to feed in nitrogen with an ammonia concentration of advantageously 100 ppm to 5%, with 250 ppm to 3% being particularly advantageous. If more than one distillation is carried out, it is preferable to introduce nitrogen in the third distillation (evaporation C04).

In addition, it is preferable that in one distillation, in particular a fourth distillation (caprolactam rectification C05), oligomers with a low molecular weight arising in the sump, which can still be cracked with an economical advantage to give caprolactam and which have an advantageous effect on the yield, are passed for renewed processing to the melt or the depolymerisation.

In addition, the liquid discharge flow from the depolymerisation, comprising inorganic salts, excess phosphoric acid, other types of polymers and oligomers, which cannot be cracked to form caprolactam, can be mixed with the residues from a refining reactor such as R02 and passed to a neutralisation step as described below based on FIGS. 1 and 2. The residue from the neutralisation which still contains organic constituents can then be passed to thermal utilisation.

High purity caprolactam is obtained by carrying out the method according to the invention. Recirculating the poor product flows produces firstly a high yield and secondly a high purity product.

Another advantage of the method according to the invention in a previously described preferred embodiment is that no fresh steam is required if all the water for steam generation or all the steam used in cracking is recycled within the process.

In another preferred embodiment described above, the method according to the invention has the advantage in that no waste flow containing a caprolactam-water mixture leaves the plant. In this way, the flow 33 described in FIG. 1 contains molten polyamide/phosphoric acid/chalk/additives, but no caprolactam. All the flows containing caprolactam can be passed back internally and processed again.

FIGS. 1 and 2 show schematically a plant for carrying out a preferred embodiment of the method according to the invention.

The following meanings are used in FIGS. 1 and 2:

| Equipment | |
|---|---|
| A01 | Gravity separator |
| A02 | Packed bed filter |
| A03 | Filter |
| A04 | Packed bed filter |
| C01 | Concentration plant |
| C02 | Evaporation plant |
| C03 | Distillation plant |
| C04 | Distillation plant |

| -continued | |
|---|---|
| C05 | Distillation plant |
| E01 | Melting plant |
| K01 | Crystallisation plant |
| K02 | Crystallisation plant |
| R01 | Depolymerisation reactor |
| R02 | Refining reactor |
| R03 | Neutralisation stage |
| W01 | Cooler |
| W02 | Evaporator |
| W03 | Evaporator |
| W04 | Superheater |
| V01/S01 | Analysis-controlled distributor |
| Material flows | |
| 1 | Polyamide 6 waste |
| 2 | Melt |
| 3 | Discharge of depolymerisation |
| 4 | Steam Polyamide 6 extraction/concentration |
| 5 | Phosphoric acid |
| 6 | Raw caprolactam/water |
| 7 | Steam |
| 8 | Condensate |
| 9 | Raw caprolactam concentrate |
| 10 | Raw caprolactam concentrate |
| 11 | Oils |
| 12 | Raw caprolactam concentrate |
| 13 | Filtered raw caprolactam concentrate |
| 14 | Additives |
| 15 | Additives + raw caprolactam concentrate |
| 16 | Separated additive |
| 17 | Raw caprolactam concentrate |
| 18 | Filtered raw caprolactam concentrate |
| 19 | Alkali |
| 20 | Steam return |
| 21 | Raw caprolactam concentrate |
| 22 | Low boiling-point substances |
| 23 | Nitrogen-ammonia stripping gas |
| 24 | Raw caprolactam concentrate |
| 25 | Raw caprolactam residue |
| 26 | Distilled, pure caprolactam |
| 27 | First runnings/intermediate product, caprolactam |
| 28 | Fractionated caprolactam |
| 29 | Caprolactam residue |
| 30 | High purity caprolactam |
| 31 | Polyamide 6 extract |
| 32 | Polyamide extract concentrate |
| 33 | Neutralised discharge |

The method according to the invention will now be described in detail based on FIGS. 1 and 2, whereby the individual features of the embodiment should be understood in that they can be applied advantageously independently of one another in the method according to the invention.

The manufacture of the high purity product for the polycondensation of Polyamide 6 and which is of the best colour and product quality which is free of byproducts which reduce the properties or usage is characterised in that the Polyamide 6 waste which is recovered by mechanical methods as shown in FIG. 1 is passed to a melting extruder E01 via the feed 1. In this extruder the Polyamide 6 waste is compacted and melted under mild thermal and mechanical conditions. In the course of operation of a production plant it has proven to be economically advantageous if the residue 25, which comes from the vacuum column C05 and which, apart from short-chain polymers, colorants and products from secondary reactions, still contains recoverable amounts of caprolactam, is not passed to a disposal system, whether this may be thermal utilisation or other processes, but is instead returned as a valuable raw material to the incoming contaminated material to increase the yield and, together with it, is added to the flow of material 2 entering the depolymerisation. The feeding of the residue 25 from the vacuum column C05 can take place after a melting extruder E01 into the feed line 2 or directly into the depolymerisation reactor R01. This method has proven to be particularly advantageous when the melting of the polyamide waste takes place under vacuum. With regard to the breakdown of the polymers and the energy consumption, another method has proven to be more advantageous economically than the method previously described when the feed of the distillation residue 25 from the vacuum column C05 occurs during the melting at a point in the extruder E01 such that the vapours entering the vacuum are not loaded. This can take place for example in the condensation zone. The fed distillation residue 25 from the vacuum column C05 reduces the melt viscosity on one hand and on the other hand promotes the breakdown of the polymer chains and eases the transport through the extruder for lower driving force.

The polyamide melt leaving the melting apparatus E01 is continually passed via the feed line 2 to the depolymerisation reactor R01 in which phosphoric acid 5 and steam 4 are fed in according to the known methods according to DE 887199, EP 0875504, DE 910056, U.S. Pat. No. 4,605,762 and JP 53-13636 at temperatures between 180° C. and 300° C. and pressures of 0.5 bar and 2 bar, whereby a breakdown of the polymer chains into oligomers and monomers takes place. As can be taken from the relevant literature, for example, Brandrup/Bittner/Michaeli/Menges "Die Wiederverwertung von Kunststoffen" (The Recycling of Plastics), pp. 513–520, Verlag Carl Hanser Munich, Vienna, 1995, caprolactam is again formed which, together with the steam and other steam-volatile constituents, leaves the reactor R01 via the vapour line 6.

During the manufacture of Polyamide 6 granulate through ring-opening polycondensation of caprolactam monomers and low molecular constituents still remain as residues in the Polyamide 6 granulate and impair the application properties. These products are extracted from the polymer by a water-extraction process which is known to the specialist. The low molecular constituents and soluble monomers contained in the extraction water are present under strong dilution and give rise to high costs for disposal as waste. During consideration of the efficiency of evaporating the low concentration solution and recirculating the concentrate, it was established that this method offered cost advantages compared to disposal as waste. This advantage increases due to the fact that the vapours 7 arising in the concentration of the caprolactam-water mixture and the energy contained in them are efficiently utilised. According to this method, this takes place in that the vapours 7 are passed as shown in FIG. 1 to the sump reboiler W03 of the column C02 for heating and the distillation of the extraction water. After the release of its thermal content, part of the condensate 8 from W03 is fed in again as reflux flow into the concentration of the caprolactam in the head of C01 and the remainder is used in the neutralisation vessel R03 for preparation of the neutralisation solution and quenching of the residue flow 3.

It was found surprisingly during the operation of a preparation plant for Polyamide 6 products that it is efficient and advantageous for the product purity of the caprolactam if the concentrate 32 from the extraction and evaporation column is passed to the depolymerisation reactor R01, since the mechanical treatment and separation according to the floatation/sedimentation/centrifuge technology does not supply the extruder E01 with one hundred percent pure Polyamide 6 and polymer completely free of disturbance materials in which, for example, portions of SBR foam backing and chalk from the treatment of carpets, soot, fabric residues and other filling materials are contained in the material flow 2. During the commercial operation of a caprolactam recovery plant, it proved advantageous to discharge these secondary constituents continuously and controlled via analyses and on-line measurements of the phosphoric acid content via the residue line 3. The monitoring and control of the mass to be discharged through analyses and on-line measurements of the phosphoric acid content in the flow has proved to be particularly advantageous with regard to the efficient operation of such a plant, because on one hand the consumption of phosphoric acid could be minimised and on the other hand the consumption of alkali for the neutralisation of the residue 3 in the reactor R03 could be minimised. In addition, by the measurement and monitoring of the nitrogen content in the material flow 3 to be discharged, the breakdown of the polymer chains and therefore the yield of caprolactam could be increased advantageously in the range of 5%–25% compared to a method of operation without monitoring the nitrogen. The previously described method has been found to be very advantageous with a caprolactam preparation plant operated with Polyamide 6 waste. In contrast to caprolactam production from pure raw materials with which no disturbance to the continuous operation can occur due to varying composition of the incoming product flow, the product quality variations resulting from the varying composition of the input material could be controlled and compensated.

The caprolactam-water mixture passed to the column C01 is concentrated by fractional distillation, whereby it has proved advantageous through the selection of the internal fittings of the column and selecting the reflux ratio in the range of 1:10 to 10:1, with 1:2 to 1:4 being particularly advantageous, a temperature in the range of 150° C. to 300° C. and 0.1 bar to 1 bar to minimise the byproducts from the mixture of disturbance materials remaining in the caprolactam sump. With regard to the purity of the caprolactam, it has proved advantageous to continuously and through analyses and online measurements monitor these secondary constituents and to control the operating conditions such as for example the temperature, pressure and reflux ratio such that the best possible removal of the byproducts is achieved. This objective is attained partly due to the fact that various parameters are set over an operating period of 1000 hours and the values measured on-line are transferred to a microcomputer for evaluation with a neuronal network program.

The product 9 leaving the column C01 still contains dispersed substances in the aqueous phase. It has been established as advantageous in obtaining raw caprolactam with good product properties to integrate a separator A01 in the line 10 in which the liquid, partly oily mixtures dispersed in the aqueous phase are eliminated and are passed as material flow 11 to further utilisation such as for example, combustion. Furthermore, it was found in the course of plant operation that passing the raw caprolactam flow 12 through a packed bed filter A02 had an advantageous effect on the colour purity.

In the following reactor R03 the treatment of the aqueous solution with additives and oxidation agents 14 occurs, as is known from the commercial manufacture of caprolactam from pure raw materials, for example, potassium permanganate for improving the colour, the acid number and the unsaturated content. In contrast to industrial production which has to control continuously and only slightly varying caprolactam quality and which can operate with permanently set additive amounts, the product properties of the caprolactam solution vary due to the sometimes extreme variations of the composition of the input polyamide. In order to take this behaviour into account measurement results of the quality monitoring, which takes place for example using FTIR, refractometers and UV spectrometers, are used on the column C01 in order to dose the type of additive and the mass of the additive added such that the lowest consumption of chemicals necessary gives the best possible raw caprolactam quality. After separation of the solids part in the separator A03, the product 17 again passes through a packed bed changeable filter A04 which has an advantageous effect on the colour purity. For further concentration of the aqueous caprolactam solution, the flow 18 is fed to a central separation stage of a rectification column C03. Here, steam is drawn off at the top according to known methods at pressures in the range of 20 mbar to 250 mbar and temperatures in the range from 100° C. to 200° C. and a reflux ratio in the range from 1:10 to 2:1, and concentration of the caprolactam occurs with the addition of alkaline neutralisation agents 19. For the optimum utilisation of waste heat and the consumption of water for cracking the polyamide it has been found advantageous to condense the vapours 20 from C03 only partially and in an amount which ensures the reflux quantity. The remaining uncondensed and hot vapours 20 are added to the material flow 4 after superheating in W04.

The concentrate 21 leaving the sump of column C03 is passed to the central section of another refractionating column C04, where components which are more difficult to boil than water are separated under pressures in the range from 0.5 mbar to 50 mbar and temperatures in the range from 115° C. to 200° C. and a reflux ratio in the range from 1:10 to 2:1. It has been surprisingly established that the product properties of the recovered caprolactam decisively improve if a nitrogen flow 23, which may also contain 100 ppm to 5% of ammonia, is passed into the lower part of the column. During the operation of a carpet recycling plant it was found to be advantageous for obtaining a low acid content and good colour purity in the material flow 24 to strip with nitrogen containing ammonia during the rectification.

In the stage C05, another rectification column, in which a water-free caprolactam melt is fed into the central part under conditions known to the specialist with reduced pressure in the range from 0.5 mbar to 50 mbar and temperatures in the range from 115° C. to 200° C. and a reflux ratio in the range from 1:10 to 2:1, caprolactam is distilled.

In the sump of the column oligomers with low molecular weight remain which can still be cracked to form caprolactam with an economical benefit and which, for an advantageous effect on the yield, are passed back as the residue flow 25 for renewed treatment in the extruder E01 or the reactor R01.

The caprolactam vapour 26 is partially precipitated in the purification stage K01 by cooling. Corresponding to the phase equilibrium, the solid precipitated first exhibits a higher degree of purity than the remaining liquid melt.

This type of purification of caprolactam in K01 and K02 is distinguished by the fact that it runs in two stages and is based on known zone and melting technology. It has been established as advantageous to carry out this crystallisation in a tubular falling film apparatus as known, for example, from the company Sulzer. The melting process, which during the known fractionated crystallisation follows the separation of crystals on a wall, supplies an initially precipitating product which is passed to the crystallisation stage K02 via the line 27. The analyser S02 is connected to this stage. As has been advantageously established in the course of operation, the analyser S01 fulfils the task of checking the visual properties of the melted product and, depending on the quality of the melt, allocating it via the valve V01 either to the depolymerisation reactor R01, column C04 or C05 or, with appropriate purity, passing it for a second time to the crystallisation K01. The sequence of the fractionated crystallisation and melting method is determined by the melting temperature of the caprolactam crystals. High purity caprolactam exhibits the highest melting point and is precipitated first on the apparatus walls, whereas the following crystal layers are slightly contaminated with the mother liquor and crystallise later. The most contaminated layers are located on the outside. After the temperature in the crystal layer falls, for example, 5° C. below the melting point of pure caprolactam, the flow of mother liquor through the crystalliser is stopped and the switchover from cooling to heating occurs. Since the impure crystals melt first, they drip down, are collected and passed to the second stage K02. After, for example, reaching a temperature of 2° C. below the melting point of pure caprolactam in K01, the discharge to K02 is stopped, the rate of heating is increased and the pure caprolactam melted down. This method known from K01 is repeated in K02 with the difference that crystals melting at the start are, dependent on the temperature, passed into other apparatus and the main product of the crystallisation K02 is passed back into the crystallisation K01. According to the invention, the product more heavily contaminated at the start of the melting process is passed to the depolymerisation reactor R01, the product with medium contamination is passed to the column C03 and the product finally precipitating is passed to the column C04 or to the purification stage K01. The analyser result and a microprocessor-controlled evaluation and closed-loop control system decide on the quantities. Once the zone melting of impure product in K01 is concluded, the melting of the remaining pure crystallisation product 25 takes place, which is stored and buffered for transfer to a polycondensation plant. This buffer is advantageous and according to the invention is also fitted with an analysis device as used for the subdivision of the premelt product 21. It is used for monitoring the acid number and colour purity and controls the release of the product for further processing in a polycondensation plant. If the purity, for example, is no longer obtained due to a too lengthy period of storage, then this analyser controls the reflux of the complete or partial content to the purification stage K01/K02.

The liquid flow 3 arising in the depolymerisation R01 contains inorganic salts, excess phosphoric acid, other types of polymers and oligomers which can no longer be cracked to form caprolactam. Since the product contains, due to the type of operation, more acid than a neutral mixture, it is mixed with the residues 12 from the reactor R02 and passed to a neutralisation stage R03. Here, base is added such that a neutral salt 33 is formed which is passed on for thermal utilisation due to its organic residual content.

EXAMPLES

Example 1

Operation of a Production Plant according to the Method as in FIGS. 1 and 2 with fibrous Polyamide 6 Recovered from Carpets.

Without reflux of the flow 25, residue from column C04, without continuous phosphoric acid and nitrogen monitoring of the product flow 3 from the depolymerisation vessel R01, without circulation of the vapours 7 from the column C01 via W03 and energy interchange of polyamide extraction water C02, without monitoring of the product properties 9 after C02 and no feedback control of the conditions in C02, without solids filtration A02 and A03, without reflux of the vapours 20 from the column C03 and usage as steam in R01, without feeding in stripping gas 23 containing ammonia into column C04, without quality analysis S01 at the melting point 27 of the fractionating crystallisation K01 and control of the reflux quantities through V01 to E01, R01, C04 and C05.

Example 2

Operation of a Production Plant According to the Method as in Example 1 after the installation of
reflux of flow 25, residue from column C04,
continuous phosphoric acid and nitrogen monitoring of the product flow 3 from the depolymerisation vessel R01.

Example 3

Operation of a Production Plant According to the Method as in Example 2 after the installation of
circulation of the vapours 7 from column C01 via W03 and energy interchange of polyamide extraction water C02,
monitoring of the production properties 9 after C02 and no feedback control of the conditions in C02,
solids filtration A02 and A03.

Example 4

Operation of a Production Plant according to the Method as in Example 3 after the installation of
reflux of the vapours 20 from column C03 and usage as steam in R01,
feeding in of stripping gas 23 containing ammonia into column C04,
quality analysis device S01 in the melt product 27 of the fractionating crystallisation K01 and control of the reflux amounts through V01 to E01, R01, C04 and C05.

Example 5

As Example 4, changed raw material.
Extrusion waste from the production of polyamide fibres.

TABLE 1

| Method | Raw Material | Polyamide 6 Content Mass % | Byproducts in Raw Material | Caprolactam Yield % | Permanganate Number Sec. | UV Transmission % | Relative Energy Consumption % |
| --- | --- | --- | --- | --- | --- | --- | --- |
| Industrial | Caprolactam | — | — | — | >1000 | >85 | — |
| Example 1 | PA6 fibres Carpet | 90 | Chalk, SBR, PP | 85 | Min. 5000 Max. 8000 | Min. 75 Max. 85 | 100 |
| Example 2 | PA6 fibres Carpet | 90 | Chalk, SBR, PP | 86 | Min. 6500 Max. 8000 | Min. 80 Max. 85 | 95 |
| Example 3 | PA6 fibres Carpet | 90 | Chalk, SBR, PP | 86 | Min. 1000 Max. 12000 | Min. 85 Max. 90 | 90 |
| Example 4 | PA6 fibres Carpet | 75–96 | Chalk, SBR, PP | 91 | Industrial | Min. 88 Max. 90 | 80 |
| Example 5 | PA6 fibres Extrusion waste | 99 | Oils, Finishes | 97 | 26000 | 99 | 65 |

The invention claimed is:

1. Method for the manufacture of caprolactam from waste containing polyamides, the method comprising:
   a) depolymerisation of the waste containing polyamides to obtain a caprolactam raw material and, where applicable, a flow containing secondary constituents or additives,
   b) at least one distillation of the caprolactam raw material to obtain caprolactam material, and
   c) at least one crystallisation of the caprolactam material obtained in step b) to obtain purified caprolactam relative to the caprolactam raw material,
   whereby at least part of the purified caprolactam obtained in step c) with a permanganate number of<10000 sec. and a UV transmission of<85% is added to the waste containing polyamides before and/or during the depolymerisation.

2. Method according to claim 1, whereby at least part of the purified caprolactam obtained in step c) with a permanganate number of<10000 sec. and a UV transmission of<85% is added to step b).

3. Method according to claim 1, whereby steps a), b) and c) are carried out continuously.

4. Method according to claim 1, whereby an acidic catalyst is added in step a).

5. Method according to claim 1, whereby secondary constituents or additives are continuously and through analysis and monitoring of the cracking acid and nitrogen content of the flow, which contains the secondary constituents or additives and is obtained in step a), discharged in a controlled manner.

6. Method according to claim 5, whereby the analysis and monitoring are carried out continuously.

7. Method according to claim 1, whereby the reaction conditions in step a) are adapted to the changing composition of the material containing polyamides.

8. Method according to claim 1, whereby the caprolactam obtained after step b) is examined through continuous analysis for its quality features, such as permanganate number, UV transmission, APHA number, alkalinity and volatile base content.

9. Method according to claim 1, whereby the caprolactam obtained after step b) is passed through at least one separator to improve at least one of permanganate number, UV transmission, APHA number, alkalinity and volatile base content.

10. Method according to claim 1, whereby additives and/or oxidation agents are added to the caprolactam obtained after step b).

11. Method according to claim 1, whereby in step b) more than one distillation is carried out and additives and/or oxidation agents are added at least once to the caprolactam obtained after the first and before the last distillation.

12. Method according to claim 1, whereby in addition a packed bed filtration is carried out before and/or during step b).

13. Method according to claim 12, whereby additives and/or oxidation agents are added to the caprolactam obtained after and/or during step b) and a packed bed filtration is carried out before and/or after their addition.

14. Method according to claim 1, wherein the caprolactam obtained from the distillation of the raw caprolactam material in step b) is distilled caprolactam.

15. Method according to claim 14, wherein the purified caprolactam of step c) is purified relative to the distilled caprolactam material of step b).

* * * * *